(12) United States Patent
Pajak

(10) Patent No.: US 6,379,921 B1
(45) Date of Patent: Apr. 30, 2002

(54) METHOD FOR FIXING AND EMBEDDING TISSUES FOR HISTOLOGICAL PREPARATIONS

(76) Inventor: Bernard Pajak, Ruc Herman 26, B-6953 Mormont, Nassogne (BE)

( * ) Notice: Subject to any disclaimer, the term of this patent is extended or adjusted under 35 U.S.C. 154(b) by 0 days.

(21) Appl. No.: 09/462,105

(22) PCT Filed: Jul. 15, 1997

(86) PCT No.: PCT/BE97/00083

§ 371 Date: Jan. 14, 2000

§ 102(e) Date: Jan. 14, 2000

(87) PCT Pub. No.: WO99/04240

PCT Pub. Date: Jan. 28, 1999

(51) Int. Cl.⁷ .......................... G01N 1/30; G01N 33/48
(52) U.S. Cl. ..................... 435/40.5; 435/40.52
(58) Field of Search ............. 435/40.5, 40.52, 435/810

(56) References Cited

PUBLICATIONS

Vitha et al., J of Histochemistry & Cytochemistry, 45(1): 89–95. Immunofluorescene detection of F–actin on low melting point wax sections from plant tissues, 1997.*

Pollard et al., J of Histochemistry & Cytochemistry, 35(11): 1329–1338. Fixation, processing and immunochemical reagent effects on preservation of T–lymphocyte surface membrane antigens in parrafin–embedded tissue, 1987.*

Beckstead, J of Histochemistry, & Cytochemistry, 42(8): 1127–1134. A simple technique for preservation of fixation–sensitive antigens in paraffin–embedded tissue, 1994.*

Capco et al., J of Cell Biology, 98: 1878–1885. A new method of perparing embeddment–free sections for transmission electron microscopy: Applications to the cytoskeletal framework and other three–dimensional networks, May 1984.*

Graham, Stain Technology, 57(1): 39–43. Improved diethylene glycol distearate embedding wax, 1982.*

Kudoh et al., J of Chromatography, 295: 187–191. Analysis of fatty acid ethoxylates by preparative high–performance liquid chromatography, 1984.*

* cited by examiner

Primary Examiner—Christopher R. Tate
Assistant Examiner—Michele C. Flood
(74) Attorney, Agent, or Firm—Birch, Stewart, Kolasch & Birch, LLP

(57) ABSTRACT

The invention concerns a method whereby a tissue is fixed by a liquid fixative, dehydrated by a liquid dehydrating agent, and infiltrated/embedded in a molten compound having a melting point higher than room temperature, wherein the method comprises the steps of fixing the tissue in a liquid fixative comprising at least a soluble zinc salt, in an aqueous buffer solution, dehydrating the fixed tissue in a liquid consisting essentially of acetone, embedding and infiltrating the dehydrated fixed tissue with a resin essentially soluble in acetone.

4 Claims, 2 Drawing Sheets

METHOD FOR FIXING AND EMBEDDING TISSUES FOR HISTOLOGICAL PREPARATIONS

BACKGROUND OF THE INVENTION

The invention concerns a method for fixing and embedding tissues for histological preparations.

DESCRIPTION OF RELATED ART

Two types of methods are currently used in this field, namely 1. slicing of frozen sections
2. slicing of fixed and embedded tissue sections.

Slicing of Frozen Sections

Freezing fulfils the dual function of fixing the tissues in the condition in which they are found and to solidify them to enable them to be sliced.

Slicing of frozen samples provides a histological material:

which exhibits substantially no molecular denaturation and thus enables good determination with respect to the nature of the molecules present which has the disadvantage that it appears in the form of thick sections, thus not enabling a microscopic examination at great magnification, and in which the morphological structure of the tissue has been greatly altered by the freezing such that, if it is possible to label the molecules, it is not possible to reliably locate the molecules thus labelled in the morphological structure of the tissue.

Finally, the slices made in the frozen tissue are then prepared and examined at room temperature, and thus a chemical fixing is still necessary after the cut.

Slicing of Fixed and Embedded Tissue Sections

In this method, the tissue is (1) first fixed, then (2) subjected to a dehydration step and finally (3) subjected to an embedding step to solidify the tissue and enable it to be cut, after which (4) the tissue is cut into fine lamellae, generally by a microtome. These lamellae are disposed on object slides and (5) these preparations are finally rid of the embedding product and rehydrated prior to the histochemical treatment.

The purpose of the fixing step (1) is to prevent substantially any physicochemical alteration of the tissue, to maintain it in the initial state in which it was collected and to thus permit determinations, in particular, immunological ones.

The purpose of the infiltration/embedding step (3) is to solidify the tissue to make it possible to make the slices as thin as possible, thus enabling a more extensive examination.

The dehydration step (2) is an intermediate step whose purpose is to replace the water present in the tissues by a compound which is itself substituted—possibly with the use of solvents—by the infiltration/embedding compound.

Step (4) provides the embedded, and thus solidified, tissue sections and step (5) finally restores the tissue more or less to its initial condition, permitting the desired analysis.

Various liquid fixatives are known for implementing the fixing step (1), such as compositions based on soluble zinc salts, various organic compounds (see e.g. EP-A-0562877), as well as acetone (see e.g. U.S. Pat. No. 5,104,640).

Various compounds, such as e.g. ethanol, methanol, isopropanol and acetone are known for the dehydration step (2) (see e.g. the article by Beckstead cited below).

For the infiltration/embedding step (3), paraffin is conventionally currently used. The disadvantage of the use of paraffin is that it is weakly soluble and consequently it is only possible to eliminate it by resorting to strong solvents and that it only melts at temperatures of 58–60° C. This is substantially higher than the physiological temperature of tissues and thus denaturing for them.

Jay H. Beckstead, in The Journal of Histochemistry & Cryochemistry ("A Simple Technique for Preservation of Fixation-sensitive Antigens in Paraffin-embedded Tissues", Vol. 42, No. 8, pp. 1127–1134, 1994) describes a method for fixing/embedding using a zinc salt fixative, together with a paraffin embedding, and comparing it, on the one hand, with known paraffin embedding methods together with other fixatives and, on the other hand, with the freezing method.

This method consists of fixing the tissues with soluble zinc salts in a buffer solution, dehydrating the tissues thus fixed by increasing concentrations of ethanol/isopropanol, eliminating the ethanol/isopropanol with xylene, infiltrating/embedding with paraffin at 58–60° C., making the slices, eliminating the paraffin with three xylene baths, followed by three isopropanol baths, and rehydrating.

Acetone—which also acts as a dehydrating agent—is known for causing a perceptible morphological denaturation of the tissues. For this reason, researchers consider it to be inappropriate for fixing when one wishes to make morphological determinations, which is quite generally the case for histological sections prepared for examination with a microscope.

Alcohols (ethanol, methanol, isopropanol, for example) are known for not perceptibly degrading morphological structures when they are used with care. They are, therefore, conventionally used for the dehydration of tissues. On the other hand, they have a marked degradation effect on molecular structures (by coagulation) and, consequently, they have disadvantages when both the molecular and the morphological structures are to be preserved, as is the case in immunological studies in situ and ex vivo in immunohistochemistry.

On the other hand, alcohols have a very great dehydrating power and, to avoid altering the morphological structure, it is necessary to carry out the dehydration by successive steps, with increasing alcohol concentrations, which obviously hampers the procedure.

Having regard to the fact that paraffin is generally of low solubility, it is necessary to provide, between the dehydration step and the embedding step, an intermediate step to eliminate the dehydrating agent with solvents such as toluene, xylene, benzene or the like, which creates denaturation problems for tissues, and toxicity, and adds still another step to the mode of operation.

Finally, impregnation with paraffin requires temperatures of ±60° C., higher than the physiological temperature, and this exerts a denaturing effect (thermal coagulation) on the molecular structures.

Moreover, the process for eliminating paraffin and rehydration of the preparations must also be done with strong solvents which are not without disadvantages.

A method is also known ("Immunofluorescence Detection of F-actin on Low Melting Point Wax Sections from Plant Tissues" by Stanislav Vitha et al, in The Journal of Histochemistry & Cryochemistry, Vol. 45(1): 09–95, 1997) that consists of fixing the tissues successively in formaldehyde and zinc chloride solutions, the latter step being carried out at 60° C., dehydrating the tissues with increasing ethanol concentrations, infiltrating/embedding, in several steps, the tissues in a resin consisting of 90% polyethylene glycol 400 distearate [which is also known under the name polyoxyethylene bis(stearate)] and of 10% 1-hexadecanol, at 35–57°, making the slices, and eliminating the resin with ethanol of technical grade, and rehydrating the preparations.

BRIEF DESCRIPTION OF THE INVENTION

According to the invention, a method for fixing/embedding is to be provided which does not perceptibly denature either the molecular structure nor the morphological structure of the tissues, to enable analysis that is as reliable and precise as possible. This is important, in particular, for immunological analysis in situ and ex vivo, in which determinations and immunological analyses are to be made not only on biological molecules extracted from their cellular and/or tissue environment, but also such molecules in this environment.

DESCRIPTION OF THE INVENTION

Figure 1A:
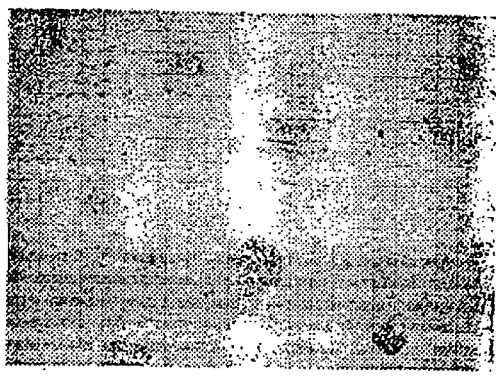
FIGS. 1A, 1B and 1C are photographs of tissue sections of a mouse spleen, obtained by freezing.

Therefore, an object of the invention is to provide a method making it possible to obtain sections of tissues which are not substantially denatured, neither from the molecular point of view, so as to enable quantitative immunological determinations, nor from the morphological point of view, to make it possible to realize these determinations in the original cellular and/or tissue environment.

The methods known in the prior art do not enable one to obtain this object insofar as they denature either the molecular structure or the morphological structure, or even both.

According to the invention, this object is attained by a method for fixing and embedding tissue for histological preparations, it being possible to implement it more or less at the physiological temperature, which essentially comprises the steps consisting of:

fixing the tissue in a liquid fixative comprising at least one soluble zinc salt, in an aqueous buffer solution, dehydrating the tissue thus fixed in a liquid consisting essentially of acetone, embedding and infiltrating the fixed and dehydrated tissue with a resin substantially soluble in any proportion of acetone.

According to another feature of the invention, the resin melts at a temperature of not higher than 37–40° C.

According to an additional feature of the invention, the resin consists of polyoxyethylene bis(stearate).

According to still another feature, the resin comprises, based of 100% by weight of the final composition, 0 to 20% by weight of a solidifying compound, comprising hexadecanol and/or diethylene glycol distearate, for the purpose of rendering it more solid at room temperature.

The invention also concerns a process for the preparation of histological sections by applying the method which comprises essentially a flask of an aqueous solution buffered with one or more zinc salts and a quantity of a polyoxyethylene bis(stearate) resin composition mixed with hexadecanol and/or diethylene glycol distearate, depending on the desired temperature of use.

According to another feature of the invention, the case also comprises an acetone flask.

The method of the invention is applicable in all fields of histology and histochemistry and its implementation is extremely simple. It can be carried out at a temperature of 35–37° C., i.e. substantially the physiological temperature of living tissue.

The polyoxyethylene bis(stearate) resin is already known from the article by S. Vitha et al.

This resin, the melting point of which is 37° C., makes it possible to make the cuts under good conditions up to temperatures of 10 to 12° C. The purpose of adding hexadecanol is to make it more solid at room temperature, in order to make it possible to make slices at the temperature in the laboratory.

According to the invention, it was also found that hexadecanol can also be replaced in whole or in part by diethylene glycol distearate which has substantially the same properties (almost inert vis-a-vis tissues, and a hardening effect on the resin).

An important feature of the method of the invention, in addition to embedding at "normal" temperature, is the association of a zinc-salt based fixative with the acetone as dehydrating agent.

Acetone does not generally appear in histology treatises (MARTOJA R. & MARTOJA M., 1967, "Initiation aux Techniques de l'Histologie Animale", ed. MASSON et Cie) as a fixative, even if it is occasionally used as a dehydrating agent. This is justified by its low penetration speed in tissues and the morphological disorders that it causes. Nevertheless, it is cited as a fixative in some cases when one is looking to preserve enzymatic activity in situ.

POLLARD et al (J. Histochem. Cytochm., 1987, 35 (11): 1329) states that molecules such as CD4 and CD8, markers of T-lymphocytes, can no more be evidenced on tissue sections fixed with acetone and embedded in paraffin even though they remain detectable on frozen sections treated with acetone for at least 30 minutes. This result appears to show that acetone itself is not denaturing but that, together with an embedding in paraffin, it no longer permits the detection of these two markers.

According to the inventor's research, the use of acetone as a fixative and dehydrating agent, and of polyoxyethylene bis(stearate) resin as an embedding environment improves the performances of fixing/embedding methods by permitting the use of a greater number of antibodies and by facilitating the making of fine cuts. In spite of this improvement, this method still does not permit the detection of molecules such as CD3, CD4 and CD8 (see Table 2), thus confirming the results of POLLARD et al. Moreover, a certain number of morphological deformations induced by acetone are observed: dilatation of the tissues, appearance of artifactual intercellular spaces.

The combination according to the invention of first fixing tissues with an aqueous solution buffered with a zinc salt, and dehydrating with acetone, followed by infiltration/embedding with a resin such as polyoxyethylene bis (stearate) completely miscible with acetone, suppresses these deficiencies.

In fact, not only the preservation of molecular tissues appears complete, but the fixing with zinc salts seems to ensure that the tissues have a morphological stabilization such that they then become resistant to deformations induced by acetone.

The subsequent embedding with a resin which is completely miscible with acetone avoids, on the other hand, the need to recover intermediary solvents to eliminate the acetone prior to embedding; this same advantage is also found later, when it is necessary to eliminate the resin and rehydrate the tissue.

For a person skilled in the art who knows the method according to S. Vitha et al, as well as the properties of acetone, and who wishes to work at room temperature while simplifying the method to a maximum, a normal process would therefore have consisted of using acetone as a fixative and dehydrating agent, thus obtaining a substantially denaturing method from the morphological point of view.

Surprisingly, the inventors discovered that the combination of fixing with zinc salts followed by dehydrating with acetone did not lead to the perceptible molecular denaturing normally produced by acetone.

Without wishing to be limited to this explanation in any way, it seems that the physicochemical fixing produced by zinc salts is such that it resists a subsequent perceptible modification with the acetone.

Thus, another significant advantage brought about by acetone lies in the acetone being, on the other hand, miscible in any proportion in the polyoxyethylene bis(stearate) resin, such that it is not necessary to have recourse to strong solvents such as, for example, benzene, toluene or xylene to enable the transition from the acetone to the resin, which again reduces denaturing, simplifies the entire method by reducing the number of steps involved and also prevents environmental and toxicity problems that might be associated with the above solvents.

The method of the invention thus ensures a perfect synergy between the different operative stages for the preparation of the histological sections, to attain the desired result, namely minimal molecular and morphological denaturing, by a method which has been remarkably simplified vis-à-vis the prior art.

Broad fields of application will be found in the preparation of histological sections with a view to immunological determinations in situ and ex vivo, by the quality of the sections that it permits.

A preferred field for the method according to the invention is immunohistochemistry. Within sections obtained by the method, it is in fact possible to detect numerous molecules such as membrane markers characteristic of cellular lines; activation markers reflecting the state of cells; cytoplasmic proteins including cytokines or antiapoptotic proteins; glycosidic residues evidenced by lectins, fragments of nucleic acids revealed by hybridization in situ or by the TUNEL reaction characterizing apoptosis. This list is not in any way restrictive and given only by way of example.

Another field of application of the method according to the invention is the replacement of conventional methods for preparing histological sections for observation under a microscope, by the overall simplification and reliability that it permits.

Example of the Procedure for Preparing Sections

The following procedure is followed:

1. Isolation of tissue
2. Fixing: small fragments of tissue (5 mm) are immersed in the liquid fixative (several ml) with zinc salts previously cooled to 4° C. and are maintained therein for 1 to 7 days at 4° C. The fixing is carried out in small pill-type glass flasks. To prevent precipitation of the zinc salts, the liquid fixative is obtained by dissolving 5% of zinc salts (acetate and chloride, in equal parts) in distilled water. This solution is then added to a tri-HCl buffer adjusted to pH 7.4, containing 0.1% calcium acetate (1 volume of zinc salt solution for 9 volumes of tri-HCl) so as to obtain a buffered solution of zinc salts at 0.5%.
3. Dehydration: the liquid fixative is eliminated and replaced immediately by pure acetone (analytical grade); the fragments are left therein for 6 to 24 hours at 4° C.;
4. Impregnation and embedding: the fragments are transferred into a pill flask maintained at 37° C. containing the liquid resin. To ensure a good impregnation, the resin bath is changed three times, each bath lasting from 10 to 30 minutes. After the third bath, the fragments are placed in a mold of appropriate size (1 to 3 cm$^3$) previously filled with liquid resin. Once immersed in the liquid resin, the fragments can be oriented there, dependent on the subsequent requirements; if necessary, the resin is maintained liquid during this operation by immersing a metal spatula heated with the flame. When the fragment is correctly oriented, the resin is allowed to cool and solidify to room temperature in a dry location. After a night to two days, the solid block of resin can be removed from the mold and prepared to be cut into fine sections.
5. The fine sections (3 to 5 $\mu$m) are formed by a sliding or rotary microtome at room temperature. Given the low melting temperature of the resin, it can become difficult to cut at temperatures above 22° C.
6. The sections are placed on microscope slides previously gelatinized or treated with polylysine. The resin being hydroscopic, it is advised against placing on a water bath. It is preferable to place them on a drop of albumenised water directly on the slide; they are spread out at room temperature until the slide is completely dried.
7. The slides thus obtained can be preserved indefinitely until the histochemical treatment.

Example of Immunohistochemical Treatment

Elimination of the resin in an acetone bath for 10 minutes

Rehydration of the sections in a PBS bath (saline phosphate buffered to pH 7.4) for several seconds (can be extended for several dozen minutes, if necessary)

Inhibition of the endogenic pseudoperoxydases (optional step if the enzymatic revelation method makes use of an enzyme other than peroxydase): incubation of the sections in $H_2O_2$ at 1 to 3% for 10 to 30 minutes. This step should, by necessity, precede all the others in order to be effective.

Saturation of the non-specific fixing sites by the "Blocking Reagent" of the firm Boehringer (Catalogue No. 1 096 176) dissolved in PBS at pH 7.4; BSA (Bovine Serum Albumin) can also be used at 1% in PBS.

Washing in PBS

Incubation of the slides with specific biotinylated antibodies diluted in the solution of the above saturating agent. The incubation conditions of the antibodies depends on each antibody; by way of example, a concentration of 10 $\mu$g/ml antibodies gives good results after incubation of one hour at room temperature.

Washing in PBS

Incubation of the sections with the biotinylated avidine-enzyme (ABC) complex; this complex exists in three different forms comprising, as enzyme, either the peroxydase, or the alkaline phosphatase, or even the oxydase glucose; the choice of enzyme is left to the user's discretion; the best results are obtained with the complexes marketed by the firm VECTOR Washing in PBS Revealing the enzymatic activity with aid of specific substrates, obtained from the firm VECTOR Washing with running city water Counter-coloration (depending on the substrate used) and assembly of preparations The primary advantages of the invention are:
1. the extreme simplification of the fixing and embedding method;
2. the simultaneous preservation of the morphological and molecular structures of the treated tissue.

Comparative examples will enable the illustration of the advantages of point 2.

The currently known methods: freezing and fixing/embedding are denaturing either for the morphology of the tissues (freezing method) or for the molecular structures (fixing/embedding method), thus hindering the recognition of the molecules by the specific antibodies, although certain fixing/embedding methods, using especially formaldehyde as fixative, permit denatured proteins to be recognized with the aid of a limited number of antibodies (antiactin, antivimentin . . . ) capable of recognizing denatured proteins.

The inherent limitations with the fixing/embedding methods result, on the one hand, from chemical denaturations induced by the fixatives themselves, by the dehydrating agents as well as by the organic solvents miscible with paraffin; on the other hand, thermal denaturations occur during insertion in the liquid paraffin at 60° C.

The use of a resin with a low melting point (37° C.) avoids the problems of thermal denaturing.

A solution for minimizing the chemical denaturations consists of restricting, at maximum, the number of denaturing substances (alcohols, solvents, . . . ) and using, for the steps preceding embedding, compounds that are completely miscible with embedding resin.

In the following Table 1, the denaturing properties of known methods are compared with the method of the invention.

TABLE I

Comparison of denaturing properties of various methods

| Method | Morphological Denaturations | Chemical Denaturations |
| --- | --- | --- |
| Freezing | strong | weak |
| Fixing/embedding with paraffin | negligible | strong |
| Acetone + resin | weak to average | weak to average |
| Method of the invention | negligible | negligible |

Examples of Denaturations

The attached figures are given to illustrate the quality of determinations carried out after treatment with the method of the invention, by comparison with other techniques.

Figure 1B:
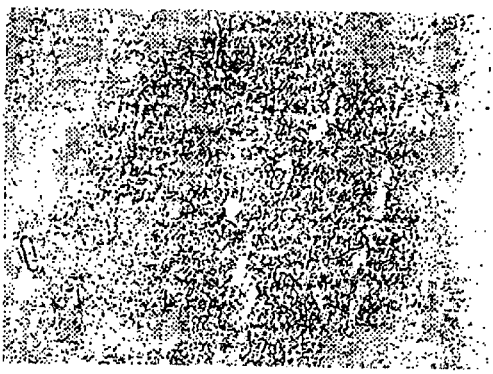
Figure 1C:
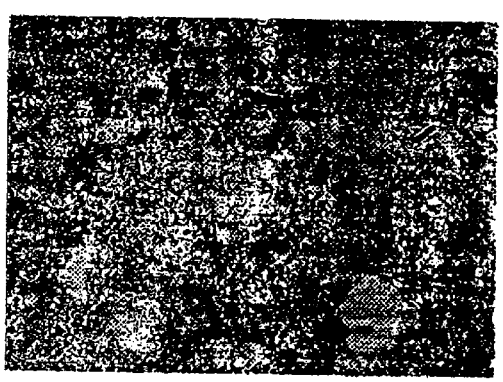

FIGS. 1A to 1C are sections, obtained by freezing, of a tissue of a mouse's spleen, with immunohistochemical marking by a biotinylated anti-B7.2 (GL1) monoclonal antibody, with revelation by alkaline phosphatase.

Figure 2A:
FIGS. 2A and 2B are similar views to FIGS. 1A, 1B and 1C after tissue preparation by another method.
Figure 2B:

FIGS. 2A and 2B are similar views, of the red pulp of spleen, after fixing/dehydration with the acetone and embedding with polyoxyethylene bis(stearate) resin.

Figure 3A:
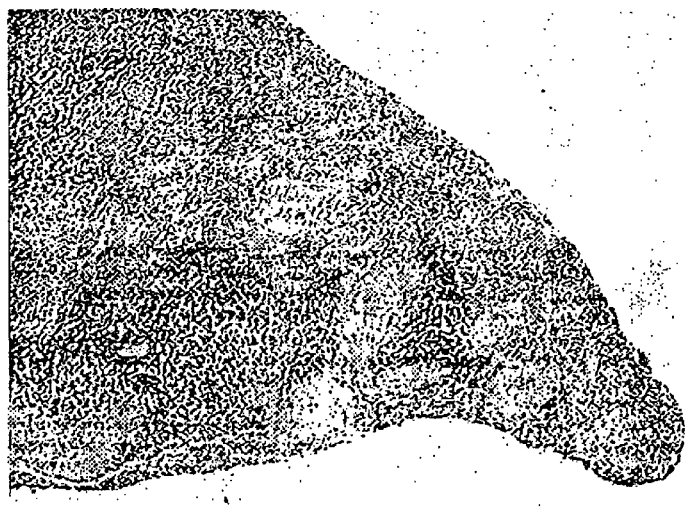
FIGS. 3A, 3B and 3C are similar views of a mouse spleen tissue section after treatment according to the present invention.
Figure 3B:
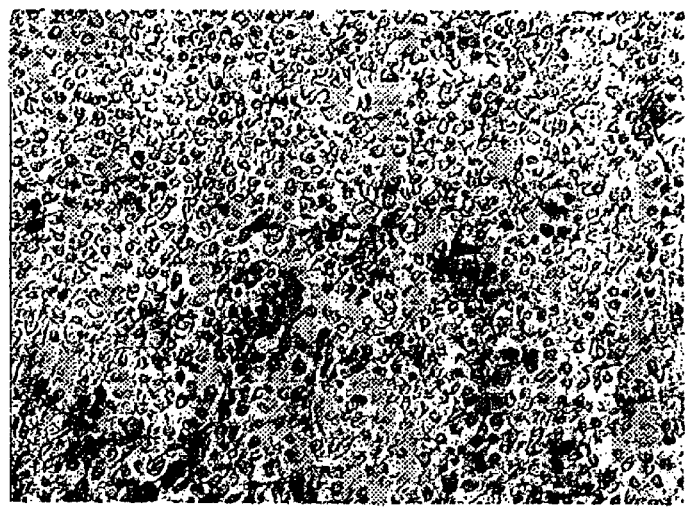
Figure 3C:
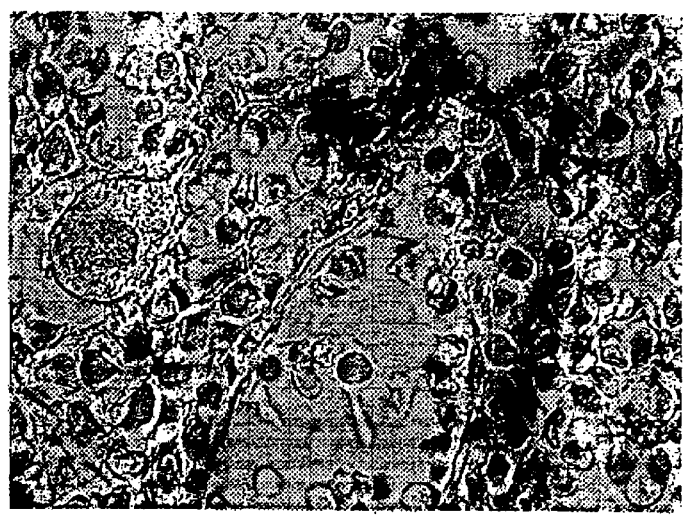

FIGS. 3A to 3C are similar views, after treatment according to the invention.

Denaturations induced by the method of cutting frozen samples are of a mechanical nature: crushing, elongation and tearing of the tissue (FIGS. 1A and 1B). They are reinforced by the difficulty of making the sections sufficiently fine in order to be able to locate, with precision, the markings obtained by the immunohistochemical treatment (FIG. 1C).

In particular:

FIG. 1A is a view at low magnification (4×), the positive cells for the marker B7.2 appear darker, FIG. 1B is a view at intermediate magnification (25×) that shows "holes" resulting from a tear during cutting, FIG. 1C is a view at high magnification (100×) showing that it is not possible to associate the marking with a precise structure.

As mentioned above, the method for fixing with acetone and embedding with resin still has disadvantages with respect to the morphological and chemical preservation. FIGS. 2 and 3 show the morphological disorders and compare then with the results obtained with the method involving fixing with zinc salts.

In particular:

FIG. 2A is a view at intermediate magnification (40×); the large artefactual spaces between the cells are noted which result from the dilatation of the tissue during fixing;

FIG. 2B is a view at high magnification (100×); the nuclei of the cells are observed as being darker, but the red blood cells can be scarcely distinguished.

FIGS. 3A and 3C illustrate perfectly the possibilities of the technique of the invention. These results could not be obtained with the freezing method (FIG. 1), nor with the method for fixing/dehydrating with acetone (FIG. 2).

In particular:

FIG. 3A is a view at low magnification (4×); one observes specific marking (darker parts) of dendritic cells (marking with an N418 monoclonal antibody, revealing with alkaline phosphatase). A counter-coloration to the green of the methyl allows one to locate the morphological structures, the nodules of the white pulp appearing clearer, and the red pulp darker, FIG. 3B is a view at medium magnification (40×) of the dendritic cells (darkest) in the white pulp in contact with the lymphocytes whose nuclei appear clearer. The absence of morphological deformation as well as the possibility of visualizing each cell is noted, FIG. 3C is a greatly magnified view (100×) of the red pulp. In addition to the dendritic cells (darker halations in the Figure), one can clearly distinguish: on the left and halfway up, a large cell of the megacaryocyte type; in the centre, in the lower part, a venous sinus in which red corpuscles can be seen, and throughout the slide, the nuclei of all of the nucleated cells.

In addition to the advantage of a perfect preservation of the morphological structures, the method for fixing/dehydrating with zinc/acetone salts, associated with embedding at a physiological temperature of 37° C., offers the possibility of detecting a greater number of molecules on sections with the aid of monoclonal antibodies. Table II gives an overview of these possibilities by comparing them with other methods.

TABLE II

Comparison of the immunohistological results obtained with the various methods

| Recognized molecules (antigens) | Antibodies | Freezing method | Fixing/ embedding with paraffin | Acetone + resin | Zinc salts + acetone + resin |
|---|---|---|---|---|---|
| B220 | | +++ | − | +++ | +++ |
| MHC-C12 | 14.4.4 | +++ | − | +++ | +++ |
| CD11b | Mac-1 | +++ | − | +++ | +++ |
| CD11c | N418 | +++ | − | +++ | +++ |
| IgD | LOMD6 | +++ | − | +++ | +++ |
| NK | 5E6 | ++ | NT | NT | +++ |
| CD3 | 7D6 | ++ | − | − | +++ |
| CD4 | RM4-5 | +++ | − | − | +++ |
| CD8 | 53-6.7 | ++ | − | − | +++ |
| Vβ8 | F23.1 | ++ | NT | NT | +++ |
| Vβ6 | | +/− | NT | NT | +++ |
| B7.2 | GL-1 | + | − | +/− | +++ |
| DEC-205 | NLDC-145 | + | − | +/− | +++ |
| I1-2 | S4B6 | +/++ | NT | − | +++ |
| I1-4 | 11B11 | +/++ | NT | − | +++ |
| INFγ | DB1 | +/++ | NT | − | +++ |
| Galβ1-4Gal | PNA | ++ | +++ | +++ | +++ |

Note: NT = not tested

In the preceding, polyoxyethylene bis(stearate) resin refers to a composition containing this compound to which the desired quantity is added (from 0 to 20% by weight overall, based on 100% by weight of the composition) of hexadecanol and/or diethylene glycol distearate, to make it more solid at room temperature. As indicated, the polyoxyethylene bis(stearate) alone is nevertheless sufficiently solid at a temperature of 10–12° C. to make it possible to obtain the desired fine sections.

In the same way, although the invention was described with only this resin, it goes without saying that it can be replaced by any resin having similar properties, namely complete miscibility with acetone, a melting temperature not higher than 37–40° C., and sufficient solidity at normal temperature, to enable one to obtain the fine tissue sections in laboratory conditions.

Finally, the invention concerns a process for preparing the histological sections that enables one to obtain said histological sections according to the method of the invention.

We claim:

1. A method for fixing and embedding a tissue for histological preparations, comprising:

fixing the tissue in a liquid fixative comprising at least one soluble zinc salt, in an aqueous buffer solution, dehydrating the fixed tissue in a liquid consisting essentially of acetone, embedding and infiltrating the fixed and dehydrated tissue, at a temperature not greater than 40° C., with a molten resin which has a melting temperature of not greater than 40° C. which is soluble in any proportion in acetone.

2. A method according to claim 1, wherein said embedding and infiltrating step is performed at a temperature not greater than 37° C.

3. A method according to claim 2, wherein said resin comprises polyoxyethylene bis(stearate).

4. A method according to claim 1, wherein said resin comprises 80% to 100% by weight of a polyoxyethylene bis(stearate) resin, and 0 to 20% by weight of at least one compound selected from the group consisting of hexadecanol and diethylene glycol distearate.

* * * * *